United States Patent [19]

Slepyan et al.

[11] 4,024,859

[45] May 24, 1977

[54] MOUTH GAG HAVING THREE DIMENSIONAL ALVEOLUS RETRACTOR ADJUSTABILITY

[75] Inventors: David H. Slepyan, Virginia Beach, Va.; Jack Nestor, Miami Beach, Fla.

[73] Assignee: Nestor Engineering Associates, Inc., Miami, Fla.

[22] Filed: Sept. 8, 1975

[21] Appl. No.: 611,440

[52] U.S. Cl. .................................. 128/12; 128/15; 128/20
[51] Int. Cl.² ........................................... A61B 1/00
[58] Field of Search .............................. 128/15–20, 128/3–14, 341–345

[56] References Cited

UNITED STATES PATENTS

| 1,319,904 | 10/1919 | Roberts | 128/15 |
| 3,747,592 | 7/1973 | Santos | 128/20 |

OTHER PUBLICATIONS

Modified Dingman Mouth Gag, by L. W. Thompson, British Jour. of Plastic Surgery, vol. 22, July 1969.

Primary Examiner—Robert W. Michell
Assistant Examiner—Henry S. Layton
Attorney, Agent, or Firm—Erwin M. Barnett

[57] ABSTRACT

A surgical mouth gag, which has a transverse bar mounting an adjustable tongue retractor centrally thereof, has a clamp means at each opposite end thereof for adjustably supporting a pair of alveolar retractors which coact with the tongue retractors to retain the jaws in a desired open position. A post support portion of each of the alveolar retractors adjust both for axial rotation and longitudinal sliding in its respective clamp. A modified post construction provides telescoping means for finger pressure adjustability.

7 Claims, 11 Drawing Figures

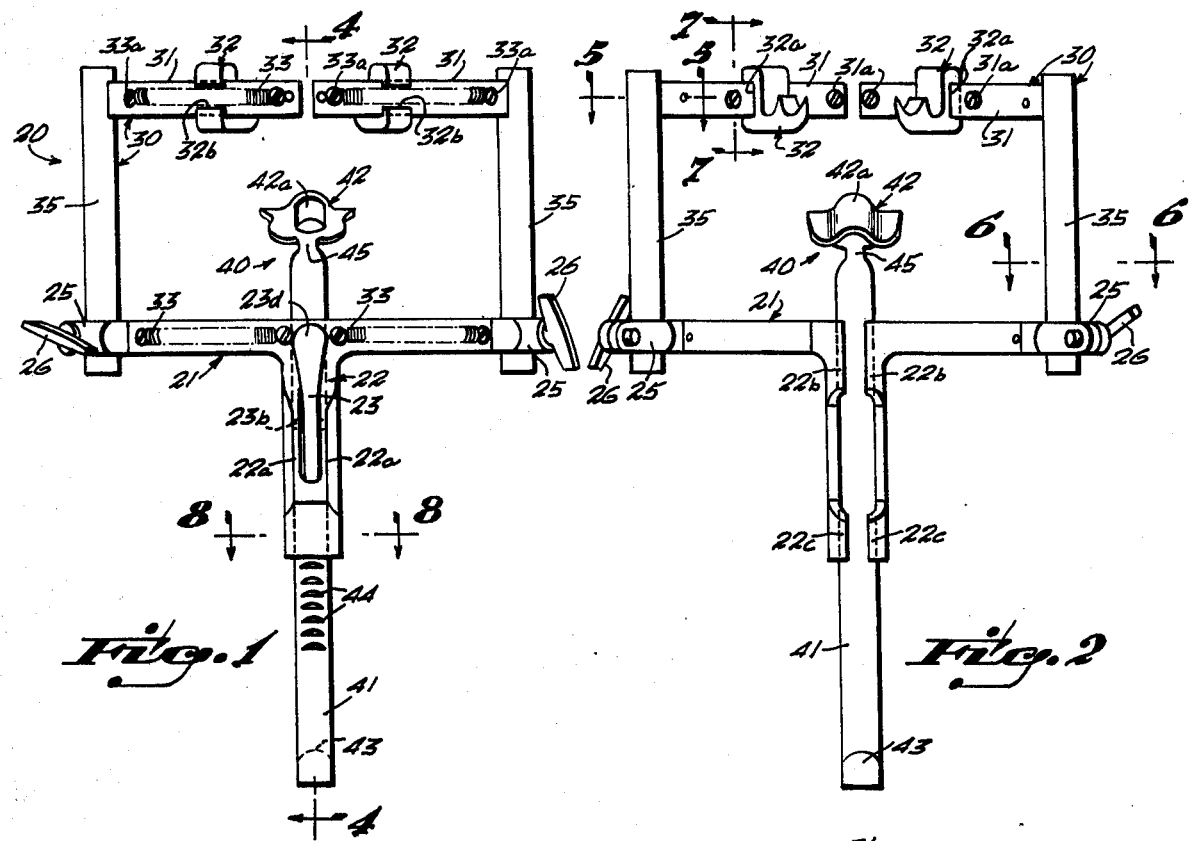
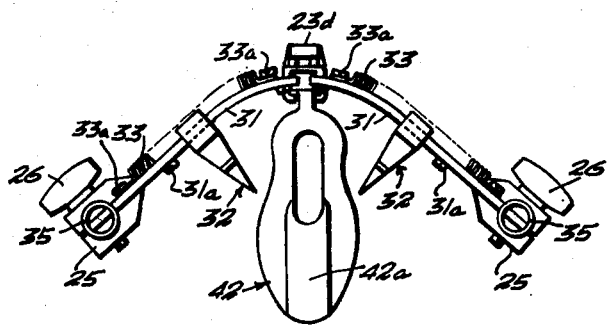
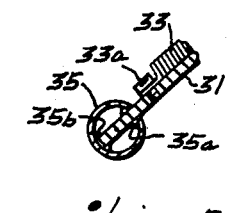
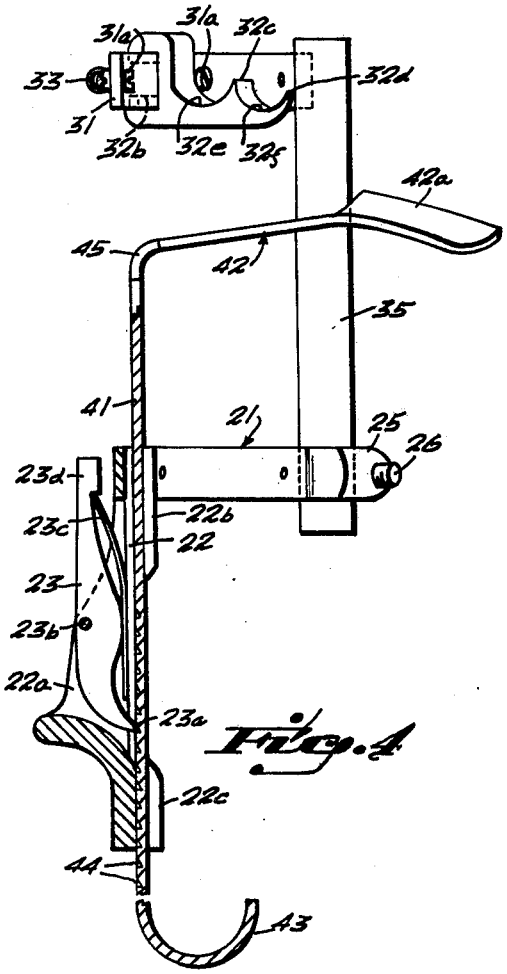

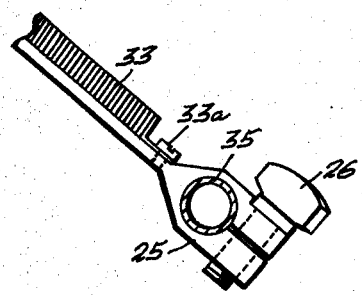
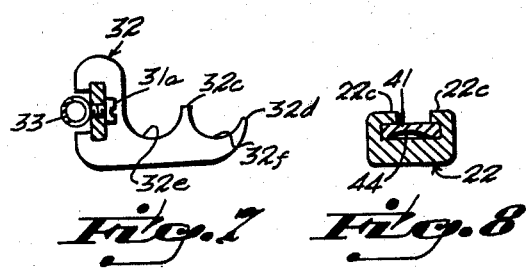
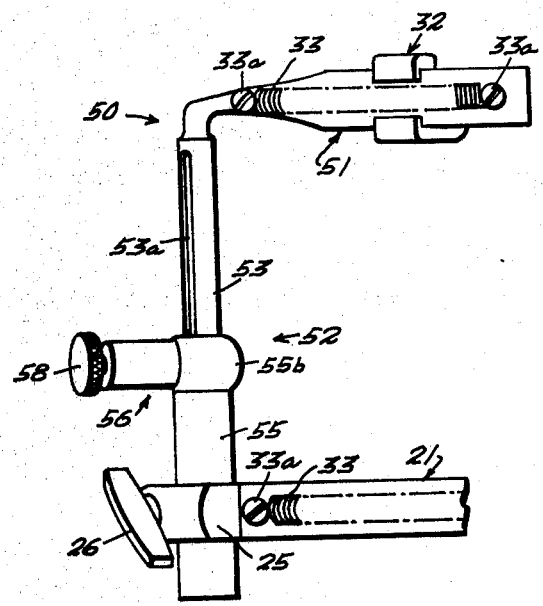
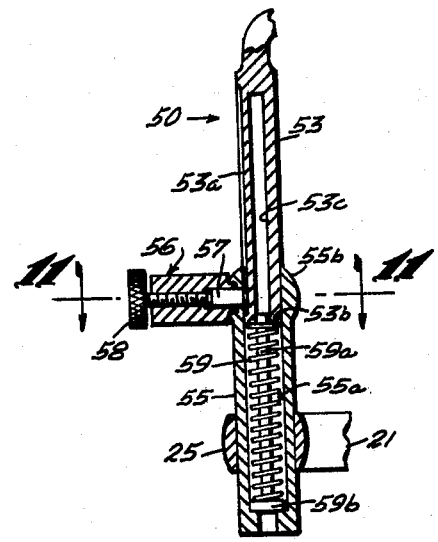
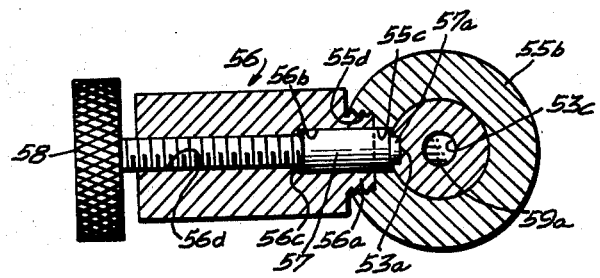

MOUTH GAG HAVING THREE DIMENSIONAL ALVEOLUS RETRACTOR ADJUSTABILITY

BACKGROUND OF THE INVENTION

1. Field of the Invention

This invention relates to surgical instruments and particularly to jaw retractors, also known as mouth gags, for positioning and retaining the jaws in a desired open position during month surgery.

2. Description of the Prior Art

The invention is an improvement of an instrument known as the Dingman mouth gag which permits adjustment in only one dimension, namely, between the alveolus retractors and the tongue retractor. Except for lateral adjustability, the alveolus retractors of the Dingman gag are mounted on an upper bar of a rigid frame to coact with the tongue retractor which is carried by a lower bar of the frame for adjustable movement toward and away from the upper bar and its relatively fixed alveolus retractors whereby separation of the jaws is determined and maintained.

There is an urgent need to correct the restrictive nature of this prior art mouth gag and provide a practical device for use in facial reconstruction involving an unstable jaw, that is, a jaw hinged at only one side due to injury to or degenerative disease of the other side and also for use where the patient's teeth and gumline are not bilaterally symmetrical.

SUMMARY OF THE INVENTION

Among the objects of the invention is to provide a jaw retractor instrument having relative three dimensional adjustability of the pair of spaced alveolus retractors as well as the ability for complete removal of either one of the alveolus retractors, where required, permitting a two point contact by the tongue retractor and the remaining alveolus retractor which provides an entire side of surgical exposure and access to the mouth.

The mouth gag comprises a transverse bar providing support for a medially mounted adjustable tongue retractor and for the supporting posts of a pair of adjustable alveolus retractors located in clamps provided at opposite ends of the bar. Each alveolus retractor has a curved bar extending medially at right angles from an upper end of the post and carries an upper jaw engaging member which is individually adjustable with respect to the other and to the tongue retractor in a horizontal direction by its sliding movement on the curved bar, in a vertical direction by axial slidinng adjustability of the supporting post in its clamp, and in a direction toward and away from the patient's face by axial rotational adjustability of the post in its clamp.

In a modified construction, the supporting post of the alveolus retractor is formed of telecscoping members and has a releasable latching device acting therebetween, whereby finger pressure against the action of an internal compression spring, which normally retains the post members in an extended condition, telescopes the post members into a shortened condition to facilitate adjustability of the upper jaw engaging member in a vertical direction.

BRIEF DESCRIPTION OF THE DRAWINGS

FIG. 1 is a front elevational view of the mouth gag embodying the invention showing the alveolus retractors in a substantially normal fully extended symmetrical position and the tongue retractor positioned midway between the upper jaw engaging members of the alveolus retractors and the base support.

FIG. 2 is a rear elevational view of the mouth gag shown in FIG. 1.

FIG. 3 is a top view as seen from FIG. 2.

FIG. 4 is an enlarged sectional view taken on line 4—4 in FIG. 1.

FIG. 5 is a fragmentary sectional view taken on line 5—5 in FIG. 2 showing details of the post and arm construction of the alveolus retractor.

FIG. 6 is an enlarged fragmentary sectional view taken on line 6—6 in FIG. 2 showing details of the clamp construction.

FIG. 7 is an enlarged sectional view taken on line 7—7 in FIG. 2 showing details of the upper jaw engaging member and its mountig on the arcuate bar.

FIG. 8 is an enlarged sectional view taken on line 8—8 in FIG. 1.

FIG. 9 is a fragmentary front elevational view of a mouth gag embodying the invention showing a modified form of alveolus retractor having a self-adjusting telescoping post.

FIG. 10 is a vertical section through the telescoping post of the mouth gag in FIG. 9 showing details of the interior structure, and FIG. 11 is an enlarged sectional view taken on line 11—11 in FIG. 10 showing details of the locking member and coaction with the telescoping post sections.

DESCRIPTION OF THE PREFERRED EMBODIMENTS

Referring in detail to the drawings, 20 generally denotes a jaw retractor, also known as a mouth gag, constructed to embody the invention, seen in FIGS. 1, 2 and 3 to comprise a base support member 21 of arcuate configuration, that is, bowed to approximate an average contour of the face below the lower lip and of a length in excess of the width of an open mouth. Base support member 21 terminates at opposite ends in split collars forming clamps 25 in which posts 35 of alveolus retractors 30 are adjustably engaged for both rotation therein and sliding movement therethrough. As seen in FIG. 6, each clamp 25 is provided with a thumb screw 26 for adjusting the clamping pressure applied to post 35 in the well understood manner.

Midway between clamps 25 and positioned to normally extend along the midline of the face, base support member 21 is formed with a slideway 22 extending at right angles thereto in which the handle portion 41 of tongue retractor 40 is removably and adjustably mounted. Handle portion 41 terminates at one end in tongue blade 42 of any well known construction and may be formed with a center channel 42a for receiving a tracheal tube (not shown) therethrough. The opposite end of the elongated handle portion 41 may be turned up to provide a finger grip 43. As seen in FIGS. 2 and 4, bend 45 between handle portion 41 and blade 42 is of a reduced width with respect to handle portion 41 permitting retractor 40 to be inserted into and removed from slideway 22. Bend 45 is sized to pass through a central slot in the rear wall of slideway 22 which rear wall is defined by two pairs of flanges 22b, 22c. Transverse notches 44 are formed in spaced relation along the outfacing surface of handle portion 41 for engagement by pointed end 23a of detent 23, which is mounted on a pivot pin 23b extending through side walls 22a of slideway 22 and is spring pressed by any suitable means such as leaf spring 23c to pivot in a counterclockwise direction as seen in FIG. 4. Each transverse notch 44 has a right angular lower wall for engagement by detent pointed end 23a and an inclined upper wall which provide uni-directional downward movement of handle portion 41 in slideway 22 in the manner and for the purpose well known in the art. End 23d of detent 23 opposite pointed end 23a is located and adapted for application of finger pressure thereto pivoting detent 23 in a clockwise direction as seen in FIG. 4 against spring 23c to disengage pointed end 23a from transverse notches 44 and release handle portion 41 for free movement through slideway 22.

Alveolus retractors 30, except for being mirror images of each other, are structurally indentical so that a description of either side applies to the other and corresponding parts are given the same reference numerals. Alveolus retractor 30 is seen to comprise a tubular post 35, an arcuate bar 31 extending from the upper end of post 35, and an upper jaw engaging member 32, which is mounted for limited sliding movement on bar 31 between projecting screw heads 31a serving as stops therefor. Bar 31 is rectangular in cross-section with its larger dimension or width parallel to the length of post 35 and is attached to the latter by any suitable means, preferably as shown in FIG. 5, as by extending through a suitable slot in post 35 to the opposite side and being welded at 35a and 35b to the interior surface at opposite points. The arcuate configuration of bar 31 corresponds to that of base support member 21 and is of a length to substantially meet the opposite bar 31 when posts 35 are rotated in clamps 25 to align both bars 31 with base support member 21 as will be clear from FIG. 3. Upper jaw engaging member 32, as seen in FIGS. 4 and 7, has an angular or L-shaped configuration with an attachment portion formed with a transverse slot 32a through which bar 31 extends, the outer wall of slot 32a being open or cutout at 32b to accommodate a relatively tightly wound coil spring 33 extending lengthwise along the outfacing surface of bar 31. Coil spring 33, which serves as a quick attachment and release means for sutures, as well known in the art, is anchored at opposite ends thereof to bar 31 by screws 33a or other suitable means. A pair of coil springs 33 are also attached by screws 33a to the corresponding outfacing surface of base support member 21. The upper jaw contacting portion of member 32 extends at right angles to slot 32a and has two spaced prominences 32c and 32d for selectively engaging the occlusal surfaces of the teeth and has curved troughs 32e and 32f providing clearance for the lips or serving to engage the gum in the absence of suitable dental structure, all in the manner well known in the art.

The practical utility and operation of mouth gag 20 will now be apparent. The various parts having been disassembled, usually to the extent that tongue retractor 40 is removed from slideway 22, but if desired, alveolus retractors 30 may also be removed from clamps 25, and properly sterilized in an autoclave, mouth gag 20 is reassembled as shown in FIG. 1, but with tongue retractor blade 42 in a fully raised position adjacent arcuate bars 31. In use, mouth gag 20 is positioned in close proximity to the patient's face so that tongue retractor blade 42 extends into the mouth and upper jaw engaging members 32 are positioned along bar 31 for contact with the upper teeth. Initially, handle portion 41 is pulled downwardly with respect to base support member 21 whereby engagement of members 32 with the upper jaw and blade 42 with the lower jaw forces the jaws apart, detent 23 permitting this downward movement while locking handle portion 41 against upward movement thereby resisting all jaw closing pressure.

Now, to achieve a desired three point contact wherein mouth gag 20 fits squarely in position and both upper jaw engaging members 32 are in operative contact with the teeth or gums, the appropriate thumb screw 26 is manipulated to permit axial sliding adjustment of post 35 to raise or lower member 32 with respect to the opposite side and/or to rotate post 35 to move member 32 inwardly or outwardly of the mouth for selective engagement by prominences 32c, 32d or troughs 32e, 32f. Where indicated one of the alveolus retractors 30 may be entirely omitted by removal of post 35 from clamp 25.

The above described relative adjustment of members 32 with respect to each other may be accomplished with the mouth only partially open and therefore under minimum tension. After achieving a desirable, well balanced, three point engagement, tongue retractor 40 may be further lowered to retain the jaws in a fully open position.

A modified form of alveolus retractor, generally designated 50, is shown in FIG. 9 used in mouth gag 20 in place of retractor 30 and is seen to comprise a telescoping post 52 having an upper inner member 53 which telescopes into a lower outer member 55, the latter having an outer dimension corresponding to that of post 35 to fit clamp 25 of base support member 21. Member 53 may be integrally formed at its upper end with right angularly extending arcuate bar 51 which corresponds in structure and function to arcuate bar 31. Bar 51 mounts an upper jaw engaging member 32 and has a coil spring 33 attached at opposite ends by screws 33a.

Upper inner telescoping member 53 is seen in FIGS. 9 and 10 as cylindrical in shape having a longitudinal groove 53a terminating short of the lower end 53b thereof and a hollow bore 53c.

Lower outer member 55 has a bore 55a sized to receive member 53 therein and is formed at its upper, inner member receiving end with a wall enlargement 55b having an opening 55c communicating with bore 55a. An outer enlarged threaded portion 55d of opening 55c is seen in FIGS. 10 and 11 engaged by threaded reduced diameter end 56a of locking member 56 which has a bore 56b aligned with opening 55c. A movable pin 57 has an end projection 57a of reduced cross-section formed with flat opposite sides and being sized and shaped to ride in longitudinal groove 53a, as seen in FIG. 12. Pin 57 is of an overall length for limited movement in bore 56b and opening 55c whereby end projection 57a is loosely retained in its engagement with groove 53a by inner shoulder 56c when pressure is released by loosening thumb screw 58 which extends through threaded bore 56d to engage pin 57. Tightening thumb screw 58 applies pressure through pin 57 to lcok inner member 53 in a desired position. Coiled compression spring 59 is coaxially positioned on an anti-kinking rod 59a within outer member bore 55a and urges upper inner telescoping member 53 and its arcuate bar 51 to a fully extended position by application of spring pressure between enlarged head 59b formed at the lower end of rod 59a and the lower end 53b of upper member 53 when thumb screw 58 is loosened to release the locking action of pin 57. The engagement of end projection 57a of pin 57 in groove 53a prevents both separation of upper member 53 from lower member 55 and relative rotation therebetween when thumb screw 58 is loose.

The self-adjusting function of alveolus retractor 50 may be utilized when positioning a mouth gag 20 so equipped between the jaws of a patient. With thumb screws 58 loosened so that each post 52 is fully expanded by the action of spring 59, mouth gag 20 may be held in both hands with posts 52 extending lengthwise between the thumbs and index fingers and pressure is applied therebetween to shorten posts 52, each to the extent that its jaw engaging member 32 carried by arcuate bar 51 is brought into alignment with the upper jaw as tongue retractor blade 42 is inserted in position on the tongue. Upon release of the finger pressure, each post 52 expands to assume its proper length in accordance with the patient's upper jaw and dental structure. Thereafter thumb screws 58 may be tightened to lock the telescoping members 53, 55 in adjusted position. When finger pressure is exerted axially at both ends of post 52, members 53, 55 readily telescope to shorten post 52, however, downward pressure on jay engaging member 32 creates a torque action between members 53, 55 which increases the friction therebetween to such a degree as to resist telescoping thereby obviating the necessity to quickly tighten thumb screws 58 after mouth gag 20 is properly aligned and positioned in the patient's mouth.

As upper telescoping member 53 telescopes into bore 55a of lower member 55 when pressure is applied against spring 59, the latter is compressed within bore 55a between head 59b of anti-kinking rod 59a and the lower end 53b of member 53 and is retained in proper axial alignment and in contact with lower end 53b as rod 59a is projected into bore 53c of upper member 53.

The jaw retractor instruments herein disclosed are seen to achieve the several objects of the invention and to be well adapted to meet conditions of practical use. As various possible embodiments might be made of this invention, and as various changes might be made in the disclosed instruments, it is to be understood that all matters herein set forth or shown in the accompanying drawings are to be interpreted as illustrative and not in a limiting sense.

What is claimed is:

1. In a jaw retractor instrument, a transverse arcuate support bar sized and shaped to conform to the face below the lips, a slideway medially located on said bar extending at right angles thereto, a tongue retractor having an elongated handle terminating at an upper end in a right angularly disposed tongue blade, said handle being removably and slidably mounted in said slideway for adjustment of said blade with respect to said support bar, and a clamp terminating each opposite end of said support bar, each of said clamps being formed to removable support in right angular relation to said support bar a cylindrical post of an alveolus retractor which has upper jaw engaging means for coacting with said tongue retractor to retain the mouth in a desired open position, each of said clamps having manual tightening means providing both axial and rotational adjustability of its said post therein, each independent of the other.

2. In the jaw retractor instrument defined in claim 1, said alveolus retractor having an arcuate bar extending from an upper end of said post and having an arcuate configuration and length corresponding to substantially one half that of said support bar, said upper jaw engaging means being mounted for limited sliding movement on said arcuate bar.

3. In the jaw retractor instrument defined in claim 2, said post being a hollow tubular structure, said arcuate bar extending through a slot formed in said post upper end, contacting an opposite interior surface thereof and being welded to the interior of said post at said slot and opposite interior surface.

4. In the jaw retractor instrument defined in claim 2, said post being formed as a two-piece telescoping structure, interior spring means urging said post into a fully extended position, and thumb screw actuated locking means coacting between the two-piece structure to secure the parts in a selected shortened condition.

5. In the jaw retractor instrument defined in claim 4, said two-piece structure including an outer lower member of an outer diameter to fit said clamp and having a bore sized to receive an upper inner member, a longitudinal groove formed in said upper inner member terminating short of the lower end thereof located within said outer member bore, said groove being engaged by said locking means to prevent separation of the members when said locking means is in a released position for telescoping movement of the post structure.

6. In the jaw retractor instrument defined in claim 4, said two-piece post structure including an outer lower member having a bore sized to receive an upper inner member, an anti-kinking rod located in said lower member bore and having an enlarged head formed at the lower end thereof, said upper inner member being formed with a bore to accommodate said anti-kinking rod therein when said two-piece structure telescopes, said interior spring means being a compression coil spring coaxially mounted abut said anti-kinking rod and being maintained thereby in operative engagement for exerting pressure between the lower end of said inner upper member and said enlarged head.

7. A jaw retractor instrument comprising a transverse arcuate support bar sized and shaped to conform to the face of a patient below the lips, a tongue retractor adjustably supported by a medial portion of said support bar to dispose a tongue blade thereof into the patient's mouth for engaging the tongue, an alveolus retractor removably and adjustably supported at each opposite end of said support bar, each alveolus retractor comprising a cylindrical post, an arcuate bar extending at right angles from an upper end of said post, and an upper jaw engaging means mounted for limited sliding movement on said arcuate bar to extend into the patient's mouth, and manually operative clamp means terminating each end of said support bar engaging each of said posts as said removable and adjustable support whereby axial rotation and axial movement of said post in said clamp means provides individual adjustability of each of said upper jaw engaging means with respect to the other in directions toward and away from the face and vertically with respect to said blade, respectively.

* * * * *